US008476039B2

(12) United States Patent
Chattopadhyay et al.

(10) Patent No.: US 8,476,039 B2
(45) Date of Patent: Jul. 2, 2013

(54) HOT SPRING BACTERIAL STRAIN BKH1 AND PROTEIN ISOLATED THEREFROM, CONCRETE COMPOSITIONS, AND USES THEREOF

(76) Inventors: Brajadulal Chattopadhyay, Kolkata (IN); Saroj Mandal, Kolkata (IN)

(*) Notice: Subject to any disclaimer, the term of this patent is extended or adjusted under 35 U.S.C. 154(b) by 522 days.

(21) Appl. No.: 12/648,297

(22) Filed: Dec. 28, 2009

(65) Prior Publication Data
US 2011/0100263 A1 May 5, 2011

(30) Foreign Application Priority Data
Nov. 4, 2009 (IN) ............................ 1311/KOL/2009

(51) Int. Cl.
| C04B 24/14 | (2006.01) |
| C12P 1/00 | (2006.01) |
| C12P 21/06 | (2006.01) |
| A61K 38/43 | (2006.01) |
| C04B 35/00 | (2006.01) |

(52) U.S. Cl.
USPC ............ 435/68.1; 106/91; 106/314; 106/737

(58) Field of Classification Search
None
See application file for complete search history.

(56) References Cited

U.S. PATENT DOCUMENTS
| 4,049,465 A | 9/1977 | Dwyer |
| 4,836,855 A * | 6/1989 | Caillau et al. ................. 106/655 |
| 6,764,543 B2 * | 7/2004 | Greenwood et al. .......... 106/737 |
| 6,989,266 B2 | 1/2006 | Koga et al. |

FOREIGN PATENT DOCUMENTS
| WO | 20050026269 A2 | 3/2005 |
| WO | 20070026352 A2 | 8/2007 |

OTHER PUBLICATIONS

Ghosh et al. 2009 Microbial activity on the microstructure of bacteria modified mortar; Cement and Concrete Composites 31:93-98.*
Day, J. L. et al., "Microbiologically Induced Sealant for Concrete Crack Remediation," pp. 1-8, Jun. 25, 2004. Retrieved from the Internet [http://replay.waybackmachine.org/20040625024852/http://www.ce.washington- .edu/em03/proceedings/papers/352.pdf].
Jasiczak, J. and Zielinski, K., "Effect of protein additive on properties of mortar," Cement and Concrete Composites, vol. 28, Issue 5, pp. 451-457, May 2006.
International Search Report and Written Opinion for PCT/IB2010/002788 mailed Feb. 24, 2011.
GenBank Accession No. 11376303, Nov. 2, 2006.
GenBank Accession No. 45069099, Mar. 4, 2004.
Altschul, S.F. et al., "Gapped BLAST and PSI-BLAST: a new generation of protein database search programs," Nucleic Acids Research, 1997, vol. 25, Issue 17, pp. 3389-402.
ASTM C597-02: Standard test method for pulse velocity through concrete. ASTM International, downloaded Dec. 17, 2012, pp. 1-4.

(Continued)

Primary Examiner — Gary Nickol
Assistant Examiner — Mary Lyons
(74) Attorney, Agent, or Firm — Foley & Lardner LLP

(57) ABSTRACT

Disclosed is a *Thermoanaerobacter* sp. bacterial strain (BKH1) isolated from a hot spring, a purified protein (bioremediase) isolated from bacterial strain BKH1, as well as concrete compositions comprising BKH1 and/or the protein, and methods of using the protein and/or composition. Also disclosed are nucleic acids encoding the protein isolated from BKH1, as well as expression vectors, host cells, cell lines, and methods for generating and purifying the bioremediase protein.

4 Claims, 8 Drawing Sheets

ESEM Pictures Of Cement Paste Samples at 28 Day Cure

A. Cement paste control

B. Protein amended cement paste

OTHER PUBLICATIONS

Bang, S. S. et al., "Calcite Precipitation Induced by Polyurethane-Immobilized Bacillus pasteurii," Enzyme Microbial Technology, 2001, vol. 28, Issue 4-5, pp. 404-409.
Belkova, L. N., "Biomineralization in Natural Environments: The Effect of Microorganisms Inhabiting Hot Spring Water and Biomats on Mineral Formation, " Geophysical Research Abstract, 2005, vol. 7, 03264, pp. 2.
Boskey, A. L., "Biomineralization: An Overview," Connect Tissue Res, 2003, vol. 44, Issue 1, pp. 5-9.
Cha, J. N. et al., "Silicatein Filaments and Subunits from a Marine Sponge Direct the Polymerization of Silica and Silicones in Vitro," Proc. Natl. Acad. SCI. USA, 1999, vol. 96, Issue 2, pp. 361-365.
Chattopadhyay, B. D. et al., "Effect of calcium ion on Methanosarcine barkeri MS," Ind. J. Expt. Biol., 1993, vol. 31, pp. 738-742.
Degraef, B. et al., "Cleaning of Concrete Fouled by Lichens with the Aid of Thiobacilli," Mat. Struct., 2005, vol. 38, Issue 284, pp. 875-882.
Dick, J. et al., "Bio-Deposition of a Calcium Carbonate Layer on Degraded Limestone by Bacillus Species," Biodegradation, 2006, vol. 17, Issue 4, pp. 357-367.
Adamson, D. A. et al., "Non-Peptide, Silicatein alpha Inspired Silica condensation Catalyst, " Polymeric Materials: Science & Engineering, 2004, vol. 90, pp. 239-240.
Edvardsen, C., "Water Permeability and Autogenous Healing of Cracks in Concrete," ACI Materials Journal, vol. 96, No. 4, pp. 448-455, 1999.
Felsenstein, J., "Confidence limits on phylogenies: an approach using the bootstrap," Evolution, 1985, vol. 39, Issue 4, pp. 783-791.
Ghosh, P., S. Mandal, and B. D. Chattopadhyay., "Effect of addition of microorganism on the strength of concrete," the Ind. Concr. J., 2006, pp. 45-48.
Ghosh, P., et al., "Use of Microorganisms to Improve the Strength of Cement-Mortar," Cement Concrete. Res, 2005, vol. 35, Issue 10, pp. 1980-1983.
Ghosh, P., et al., "Development of bioconcrete material using an enrichment culture of novel thermophilic anaerobic bacteria," Indian Journal of Experimental Biology, 2006, vol. 44, pp. 336-339.
Ghosh, S., et al., "Use of Hot Spring Bacteria for Remediation of Cracks and Increment of Durability of Structures, " The Ind. Concrete J., 2008, pp. 11-16.
Inagaki, F., et al., "Microbial Silica Deposition in Geothermal Hot Water, " App. Microbiol. Biotechnol., 2003, vol. 60, Issue 6, pp. 605-612.
Is 8112. 1989. Specification for 43-grade Ordinary Portland Cement, Bureau of Indian Standard, New Delhi, India, May 1990, 22 pages.
Is 650. 1991. Specification for standard sand from natural sources of Ennor, Tamilnadu District, India for concrete, Bureau of Indian Standard, New Delhi, India, May 1991, 8 pages.
Jonkers, H. M., Self Healing Concrete: A Biological Approach, p. 195-204. In S. van der Zwaag (ed.), Self Healing Materials: An Alternative Approach to 20 Centuries of Material Science, 2007, pp. 195-204, Springer, The Netherlands.
Kessler, M.K., et al., "Self -Healing Structural Composite Material," Compos Part A. Applied Science and Manufacturing, 2003, vol. 34, Issue 8, pp. 743-753.
Kimura, M., "A simple method for estimating evolutionary rates of base substitutions through comparative studies of nucleotide sequences, " J. Mol. Evol., 1980, vol. 16, pp. 111-120.
Lowry, O.H., et al., "Protein Measurement with the Folin Phenol Reagent, " J. Biol. Chem, 1951, vol. 193, pp. 265-75.
Ramchandran, et al., "Remeditation of Concrete Using Microorganisms," ACI. Mater. J, vol. 98, Issue 1, Jan./Feb. 2001, pp. 3-9.
Navarro, C.R., et al., "Conservation of Ornamental Stone by Myxococcus Xanthus —Induced Carbonate Biomineralization, " Appl. Environ. Microbiol, 2003, vol. 69, Issue 4, pp. 2182-2193.
Amsaleg, R., et al., "Extraction and purification of microbial DNA from soil and sediment samples, " 2001, Appl. Soil Ecol, vol. 18, Issue 1, pp. 47-60.
Saitou, N, and Nei, M., "The Neighbour-Joining Method: a new method for reconstructing phylogenetic trees, " Mol. Biol. Evol, 1987, vol. 4, pp. 406-425.
Schröder, H.C., et al., Silicase, an enzyme which degrades biogenous amorphous silica: contribution to the metabolism of silica deposition in the demosponge Suberites domuncula, Prog. Mol. Subcell. Biol, 2003, vol. 33, pp. 249-268.
Skinner, W. C. H, and H. A. Jahren., Biomineralization, p. 117-184. In W. H. Schlesinger (ed.), Treatise on Geochemistry, vol. 8. Elsevier, 69 pages 2007.
Vrieling, E. G., et al., "Controlled silica synthesis inspired by diatom silicon biomineralization, " J. Nanoscience and Nanotechnology, 2005, vol. 5, Issue 1, pp. 68-78.
Weiner, S, and M. P. Dove., "An Overview of Biomineralization Processes and the Problem of the Vital Effect in Biomineralization, " Review in Mineral Geochem, 2003, vol. 54, pp. 1-29.
White, S.R., et al., "Autonomic Healing of Polymer Composites," Nature, 2001, vol. 409, pp. 794-797.
Chattopadhyay, B.D., et al., "Inhibitory role of aluminium in methane emission in rice field, "Indian Journal of Experimental Biology, 1994, vol. 32, pp. 495-500.
Needleman, S.B and Wunsch, C.D, "A general method applicable to the search for similarities in the amino acid sequence of two proteins, " J. Mol. Bio1,1970, vol. 48, Issue 3, pp. 443-453.
Henikoff, S and Henikoff, J.G., "Amino acid substitution matrices from protein blocks," Proc. Natl. Acad. Sci. USA, 1992, vol. 89, pp. 10915-10919.
Dayhoff., et al., "Atlas of Protein Sequence and Structure, " National Biomedical Research Foundation, Washington, DC, 1978, vol. 5, supp. 3, pp. 73-93.
Atschul, S.F., et al., "Basic local alignment search tool, "J. Mol. Biol, 1990, vol. 215, pp. 403-410.
Devereux, J., et al., A comprehensive set of sequence analysis programs for the VAX, Nucleic Acids Research, 1984, vol. 12, Issue 1, pp. 387-395.
Carillo, H., and Lipman, D., The multiple sequence alignment problem in biology, SIAM J. applied Math., 1988, vol. 48, Issue 5, pp. 1073-1082.
Studier, J.A., and Keppler, K.J., A note on the neighbor-joining algorithm of saitou and nei, Mol. Biol Evol, 1988, vol. 5, Issue 6, pp. 729-731.
Gascuel, O and Steel, M., "Neighbor-joining revealed," Mol Biol Evol, 2006, vol. 23, Issue 11, pp. 1997-2000.

* cited by examiner

FIGURE 1. SEM Views Of The Bacterial Strain BKH1
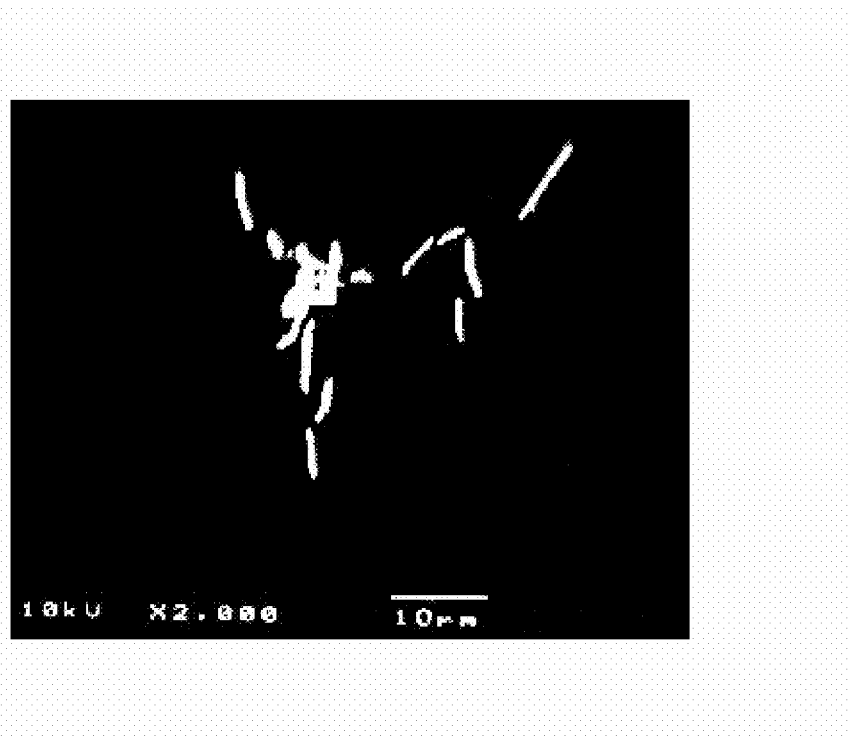
A
B
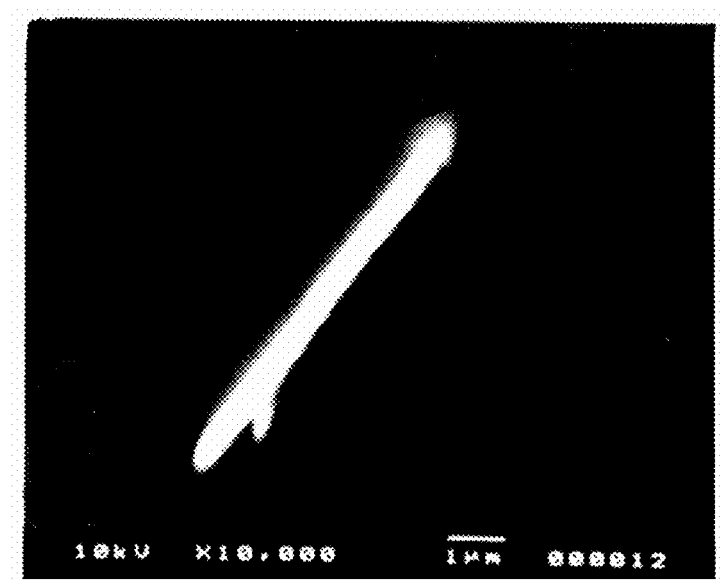

FIGURE 2. Phylogenetic Tree Of BKH1 By Neighbor Joining Method

FIGURE 3. SDS-PAGE Analysis Of Bioremediase
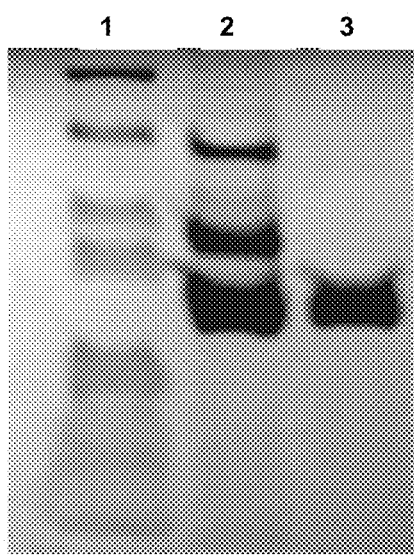

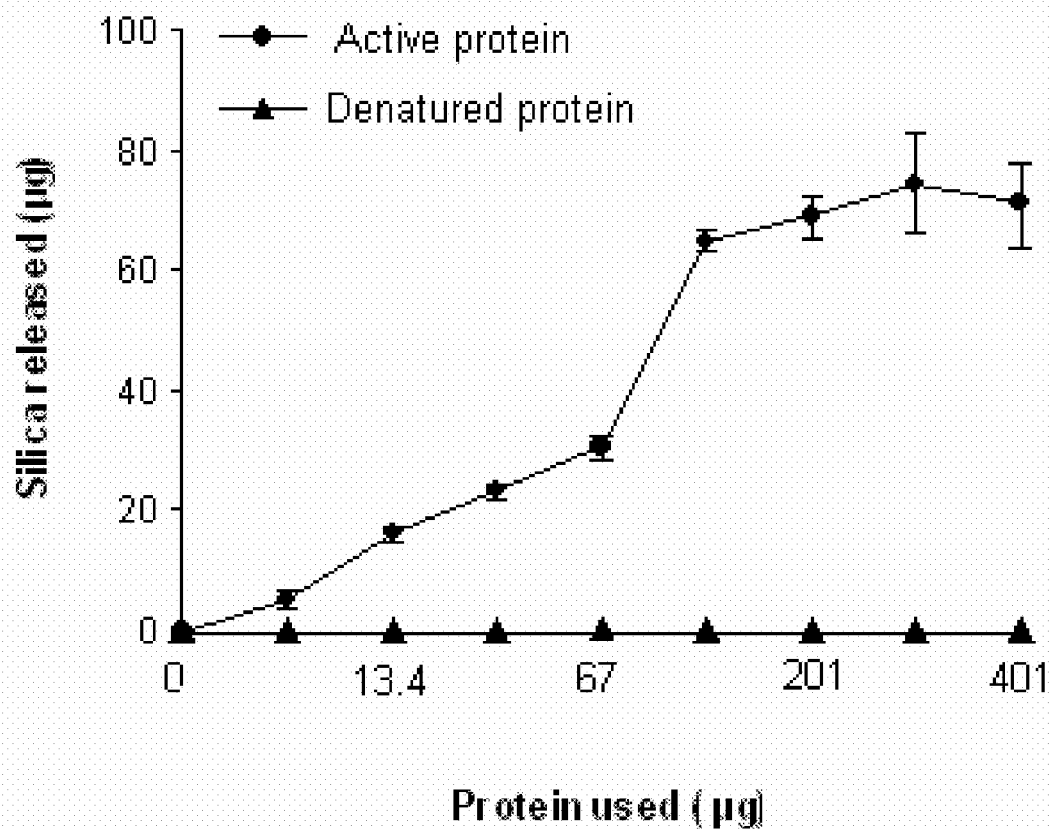

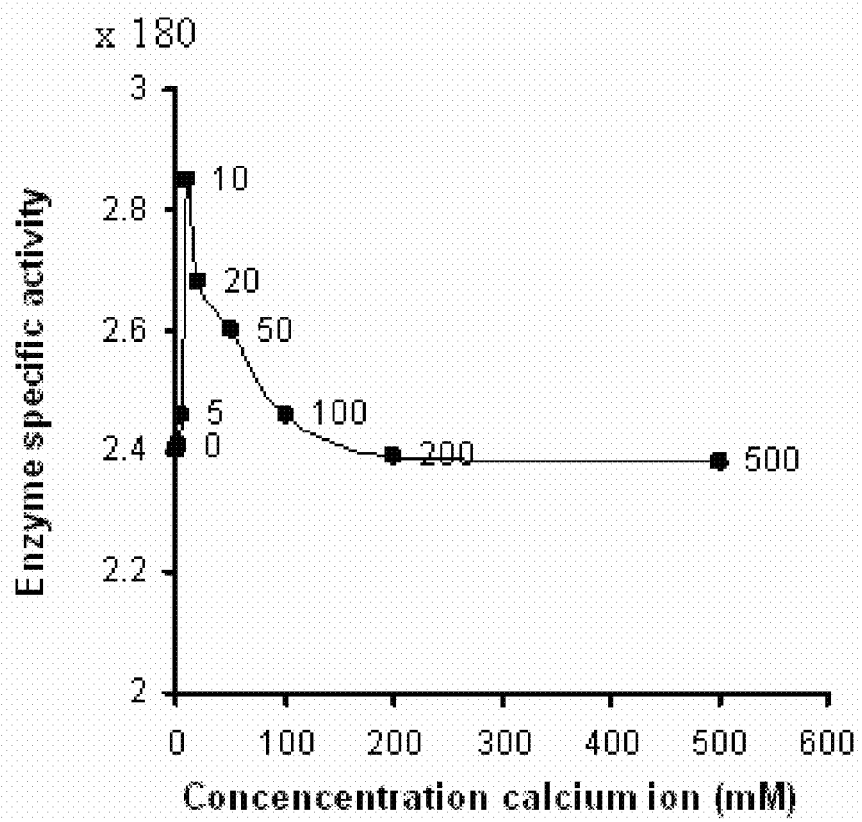

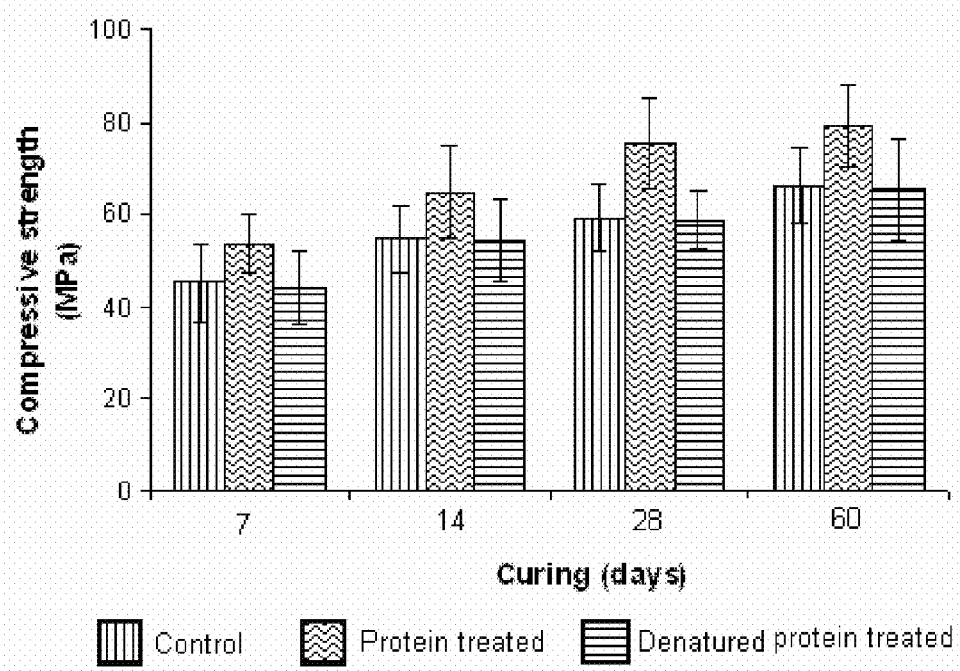

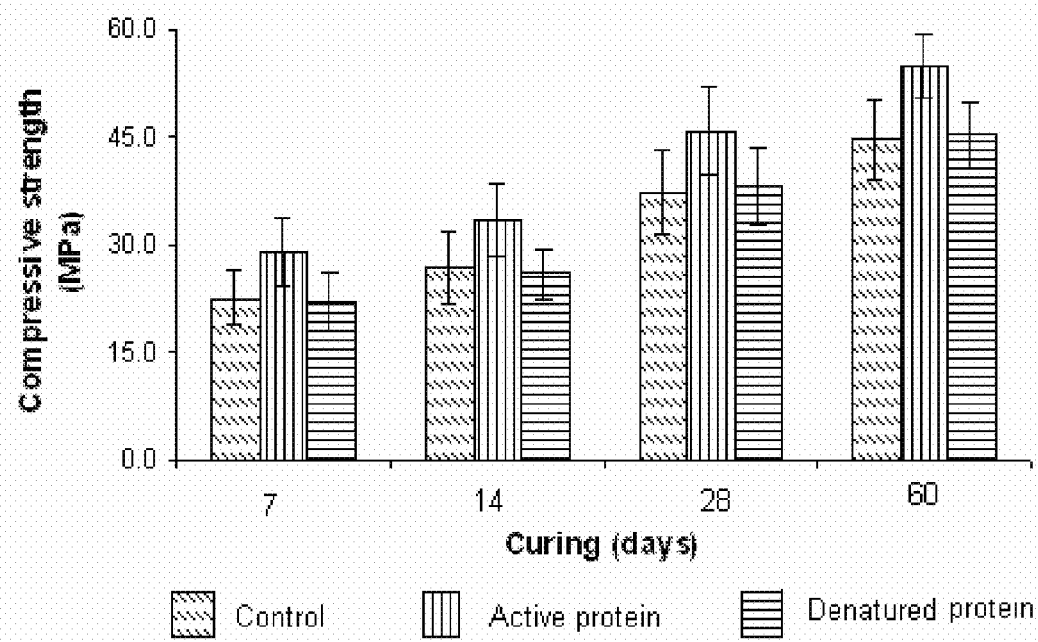

FIGURE 6. ESEM Pictures Of Cement Paste Samples at 28 Day Cure
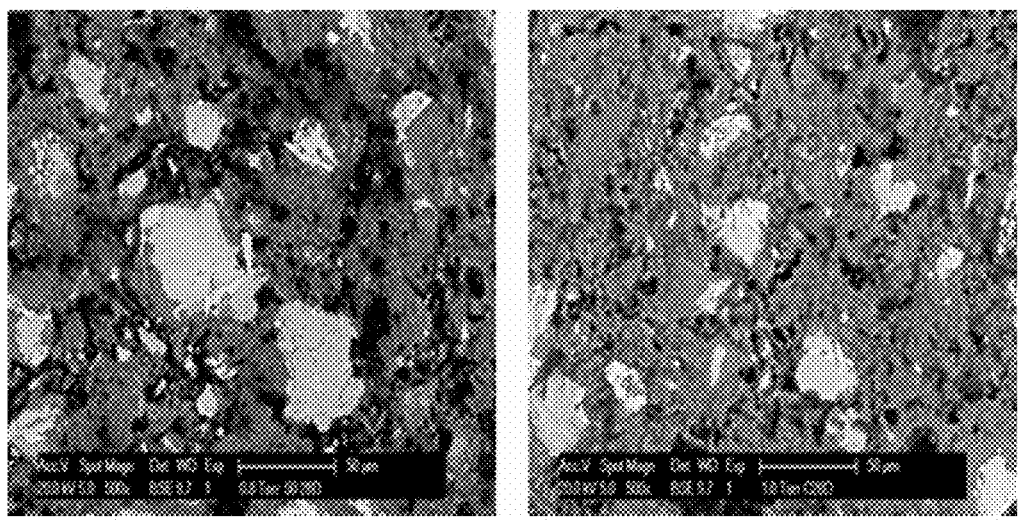
A. Cement paste controlB. Protein amended cement paste

HOT SPRING BACTERIAL STRAIN BKH1 AND PROTEIN ISOLATED THEREFROM, CONCRETE COMPOSITIONS, AND USES THEREOF

CROSS-REFERENCE TO RELATED APPLICATION

This application claims priority under 35 U.S.C. §119(d) to a corresponding patent application filed in India, having application number 1311/KOL/2009, filed on Nov. 4, 2009, the entire contents of which are herein incorporated by reference.

BACKGROUND

Concrete is a mechanically strong artificial rock-like material that is the most widely used construction material in the world. However, due to the heterogeneity of the composition of its principal components, cement, water and a variety of aggregates, the properties of the final products can vary widely. Concrete is characterized by a high compressive strength, but it also has a relatively low-tensile strength. Its lack of tensile strength can be compensated for through the use of reinforcements (e.g., steel rebar) that can increase the concrete's resilience to tensile forces. Even when reinforced, however, concrete materials can crack as a result of applied structural loading, shrinkage, and thermal deformations, any of which are practically inevitable and often anticipated in restrained conditions. Corrosion of the concrete reinforcements and crack formation are major causes of degeneration, which consequently limit the durability and lifetime of a concrete structure. For example, the presence of cracking reduces the load capacity and stiffness of a concrete structure. Cracks also provide pathways for the penetration of ions that can cause concrete to deteriorate. Chloride ion, oxygen, and carbonating agents can migrate through cracks and lead to corrosion of reinforcing steel which is the major cause of concrete deterioration world-wide. Therefore, the formation of cracks is a dominant form of damage in concrete materials. Consequently, large amounts of time and money are directed to finding ways to improve the quality and durability of concrete, as well as to finding ways to decrease its manufacturing costs.

Early research performed by White and co-workers focused on the ability of materials to self-heal. [White, S. R., et al., *Nature* (2001) 409:794-797]. They "report a structural polymeric material with the ability to autonomically heal cracks [that] incorporates a microencapsulated healing agent that is released upon crack intrusion. Polymerization of the healing agent is then triggered by contact with an embedded catalyst, bonding the crack faces [and yielding] as much as 75% recovery in toughness" (see, Abstract). Similar self-healing mechanisms are known in concrete materials. It has been proposed that the primary self-healing process in high performance concrete derives from the formation of calcium carbonate resulting from unhydrated cement particles coming in contact with permeating water carrying dissolved carbon dioxide.

In recent years, there has been an increased amount of research focused on the process of biomineralization and its effect on mechanical property recovery in concrete materials. Biomineralization is a metabolic process that takes place in certain microorganisms and results in the formation of hard structures, surfaces, or scale by combining minerals with organic compounds. Certain microorganisms found in hot springs are known to participate in biomineralization processes, which play an important role in the proper functioning of these geothermal ecosystems. Several researchers have explored the concept of biomineralization in an attempt to develop bio-concrete compositions and materials with self-healing properties. For example, Bang, et al. showed that "[*Bacillus pasteurii*] immobilized cells exhibited the rates of calcite precipitation and ammonia production as high as those of the free cells" and that the calcite "showed little effect on the elastic modulus and tensile strength of the polymer, but increased the compressive strengths of concrete cubes, whose cracks were remediated with . . . immobilized cells" (see Abstract). Similarly, Rodriguez-Navarro et al. demonstrated that "*Myxococcus Xanthus*-induced calcium carbonate precipitation efficiently protects and consolidates porous ornamental limestone" and that "new [calcium carbonate] crystals are more stress resistant than the calcite grains of the original stone because they are organic-inorganic composites" (see Abstract). Certain microorganisms have found use in concrete technology such as, for example, cleaning agents for concrete surfaces. [DeGraef, B., et al. (2005)]. Other studies have explored bacterial bio-deposition of calcium carbonate for the treatment degraded limestone. [Dick, J., et al. (2006)].

SUMMARY

In one aspect the application provides an isolated protein comprising the amino acid sequence DFPIANGERQ SPVDIDTKAV VQDPA (SEQ ID NO:1), wherein the protein has silica releasing activity of about 70 μg silica/mg protein.

In another aspect the application provides an isolated protein comprising an N-terminal amino acid sequence (N-term)—DFPIANGERQ SPVDIDTKAV VQDPA (SEQ ID NO:1).

In an aspect the application provides a concrete composition comprising a cement matrix and an amount of bacterial cells of strain BKH1.

In an aspect the application provides a concrete composition comprising a cement matrix and a protein comprising the amino acid sequence: DFPIANGERQ SPVDIDTKAV VQDPA (SEQ ID NO:1).

In an aspect the application provides a method for isolating bioremediase protein comprising SEQ ID NO:1, wherein the method comprises: (a) culturing *Thermoanaerobacter* sp. BKH1 cells under conditions that allow for cell growth; (b) collecting the growth medium from the culturing from (a); (c) lyophilizing the growth medium from (b) to dryness; (d) dissolving the lyphilisate generated in (c) in a solvent; (e) contacting the solution generated in (d) with acetone in an amount to generate protein precipitate; (f) contacting the protein precipitate from (e) with solvent; and (g) isolating the proteins in the solution from (f) based on molecular weight; wherein the bioremediase protein comprises a molecular weight of about 28 kDa.

In an aspect the application provides an isolated *Thermoanaerobacter* sp. bacterial cell of strain BKH1, wherein the BKH1 strain comprises a 697 nucleotide 16S ribosomal RNA sequence of:

```
                                                        (SEQ ID NO: 2)
ggtaagcacg gagttgagtg ccggatagcg gcggacgggg tgagtaaacg cgtgggcaaa cctaccctta agaccgggga taacacctcg aaaggggtgc taatactgga taagctcctt gtagggcatc ctatgaggag ggaaggtagc ggaagctacc gcttaaggat gggcccgcgt cccatcagct agttggtagg gtaacggcct accaaggcga cgacgggtag ccggcctgag agggtggtcg gccacactgg gactgagaca cggcccagac tcctacggga ggcagcagtg gggaatcttg cgcaatgggc gaaagcctga cgcagcgacg ccgcgtgagc gaagaaggcc ttcgggtcgt aaagctcgat agtgtgggaa gaatagatga cggtaccaca cgaaagcccc ggctaactac gtgccagcag ccgcggtaag acgtaggggg cgagcgttgt ccggaattac tgggcgtaaa gggcgcgtag gcggccactt aagtcaggtg taaaaaaccc gggctcaacc cgggggatgc acatgaaact gggtggctag agggcaggag aggggagtgg aattcccggt gtagcggtga aatgcgtaga tatcgggagg aataccagtg gcgaaggcga ctctctggac tgaccctgac gctgaggcgc gaaagcgtgg ggagcaa.
```

In an aspect the application provides an isolated nucleic acid molecule encoding a protein comprising the amino acid sequence DFPIANGERQ SPVDIDTKAV VQDPA (SEQ ID NO:1), wherein the protein has silica releasing activity of about 70 μg silica/mg protein.

In an aspect the application provides an expression vector comprising an nucleic acid molecule encoding a protein comprising the amino acid sequence DFPIANGERQ SPVDIDTKAV VQDPA (SEQ ID NO:1), wherein the protein has silica releasing activity of about 70 μg silica/mg protein.

In an aspect the application provides a host cell comprising the above-described expression vector.

In an aspect the application provides a method for increasing the strength of a concrete composition comprising contacting a cement matrix with an amount of bacterial cells of strain BKH1 effective to increase the strength of the concrete composition by about 25% relative to the strength of the concrete composition in the absence of the BKH1 bacterial cells.

In an aspect the application provides a method for increasing the strength of a concrete composition comprising contacting a cement matrix with an amount of a protein comprising the amino acid sequence: DFPIANGERQ SPVDIDTKAV VQDPA (SEQ ID NO:1) effective to increase the strength of the concrete composition by about 25% relative to the strength of the concrete composition in the absence of the protein.

In certain aspects the application provides methods for reinforcing or repairing an existing concrete structure comprising contacting the existing concrete structure with the concrete compositions described herein.

Additional aspects of the application and various embodiments of these aspects will be apparent to one of skill in the art in light of the following detailed description.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 1 (A) depicts a scanning electron micrograph (SEM) image (×2000) of the hot spring bacterium strain designated BKH1; (B) is an enlarged view (×10,000) of the same BKH1 strain.

FIG. 2 depicts a schematic representation of the phylogenetic tree for bacterium BKH1 that was generated using the Neighbor Joining Method (see, e.g., Gascuel O, Steel M., *Mol Biol Evol* (2006); 23 (11): 1997-2000; Saitou N, and Nei M. "The neighbor-joining method: a new method for reconstructing phylogenetic trees". *Mol Biol Evol* (1987); 4(4): 406-425; and Studier J. A., and Keppler K. J., *Mol Biol Evol* (1988); 5(6): 729-731.).

FIG. 3 depicts an SDS-PAGE of the purification of bioremediase protein. Lane 1—protein molecular weight standards (116 kDa; 66.2 kDa; 45 kDa; 35 kDa; 25 kDa; 18.4 kDa; 14.4 kDa; Sigma); Lane 2—supernatant protein from growth medium; Lane 3—purified bioremediase protein.

FIG. 4 (A) shows the silica release activity of the purified bioremediase protein relative to denatured protein. All values are statistically significant at $P<0.05$, ($n=6$). (B) shows the silica releasing activity of bioremediase as a function of salt ($Ca^{2+}$) concentration.

FIG. 5 (A) shows the effect of bioremediase (in active and denatured form) on cement-paste compressive strength, relative to control. The protein to cement ratio was 1 (μg/g). The values are given mean±S.D. ($n=25$); all values are statistically significant at $P<0.05$ (B) shows the effect of bioremediase (in active and denatured form) on mortar compressive strength, relative to control. The protein to cement ratio was 1 (μg/g). The values are given mean±S.D. ($n=25$); all values are statistically significant at $P<0.05$.

FIG. 6 is an environmental scanning electron microscope (ESEM) image of bioremediase-amended cement paste sample (6A) and cement-paste only control (6B) sample after 28 day curing.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The application relates generally to an isolated anaerobic bacterial cell, a protein purified from the bacteria, cement compositions, and methods that can generate a self-healing concrete material having the same physical properties as typical concrete, such as prepared using silica fumes, but at a fraction of the cost. Typically, the primary components of concrete/mortar matrix are calcium hydrate silicate (CSH), calcium hydrate (CH), capillary pores and unhydrated cement particles. The CSH component plays a key role for improving the strength and properties of the concrete. It is formed by the reaction of water with different phases like calcium hydroxides, calcium silicate etc. of cement particles. In normal concrete, more than 25% of the cement particles remain in unhydrated form. By increasing the amount of hydration in the unreacted cement particles additional CSH can be formed and will consequently increase the strength and overall properties of concrete.

An embodiment relates to an ecofriendly and self-healing bioconcrete composition. A bacterial strain, BKH1, isolated from hot springs at Brakreshwar, India has been isolated and characterized and can confer increased strength and self-healing properties to concrete when it is combined with a cement matrix. A novel protein, bioremediase, has been isolated from the BKH1 bacterial strain which can also confer increased strength and self-healing properties to concrete structures when it is combined with a cement matrix.

Thus the embodiments described herein provide several advantages over known concrete compositions. Of the many advantages, several particular advantages include:

(a) Decrease of costs: The BKH1 bacterium can be grown cheaply, in water with minimal culture growth material, which results in cheaper manufacturing costs relative to commonly used methods.

(b) Robustness: The isolated BKH1 cell and/or bioremediase protein are thermostable and maintain biomineralization activity over a wide pH range (about 6 to about 13). Also, the bacterium grows in anaerobic conditions, meaning that it (or the isolated protein) can be included throughout the entire concrete material of any structure and maintain its activity. Further, as a thermophilic organism, the BKH1 bacteria and/or the isolated bioremediase protein, can function at elevated temperatures.

(c) Environmental: The process for generating the cement, mortar, and concrete composition is eco-friendly and does not generate environmental pollutants that are associated with typical manufacturing processes.

(d) Self-healing & Efficient Compositions: The BKH1 bacteria, or the isolated bioremediase protein can recruit any unreacted cement particles that may exist within the cement matrix of the concrete composition and utilize the particles to improve the physical properties of the material, meaning that there is no need for additional cement or concrete material.

DEFINITIONS

All scientific and technical terms used throughout the application should be understood to have their common scientific/technical meaning, unless specifically indicated otherwise. Similarly when the singular form of a term or article is used, it should be understood to also encompass the plural form of that term or article.

The term "BKH1" refers to a recently discovered anaerobic bacterial strain of type *Thermoanaerobacter* sp. isolated from hot springs at Brakreshwar, India. The BKH1 cells have biomineralization activity and comprise comprises a 697 nucleotide 16S ribosomal RNA sequence of SEQ ID NO:2, (GenBank Accession No: FJ177512.1).

The term "bioremediase" or "bioremediase protein" refers to a protein that was discovered in the BKH1 bacterium. The bioremediase protein has biomineralization activity and comprises an amino acid sequence of SEQ ID NO:1, with an overall molecular weight of about 28 kDa. Protein variants and active protein fragments of the bioremediase protein are typically encompassed by the term. Variants include amino acid insertions, deletions, and substitutions, or combinations thereof, which retain a functional activity of the native bioremediase protein. Substitution variants comprise at least one amino acid residue in the native bioremediase sequence removed and a different amino acid inserted in its place at the same position. The substitutions may be single, where only one amino acid in the molecule has been substituted, or they may be multiple, where two or more amino acids have been substituted in the same bioremediase sequence. Similarly, deletion (and insertion) variants comprise at least one amino acid residue in the native bioremediase sequence removed and not replaced (or inserted).

The terms "amino acid," "amino acids," and "amino acid residues" refer to all naturally occurring L-amino acids. This definition is meant to include norleucine, ornithine, and homocysteine. The naturally occurring L-amino acids can be classified according to the chemical composition and properties of their side chains. They are broadly classified into two groups, charged and uncharged. Each of these groups is divided into subgroups to classify the amino acids more accurately: A. Charged Amino Acids—(A.1. Acidic Residues): Asp, Glu; (A.2. Basic Residues): Lys, Arg, His, Orn; B. Uncharged Amino Acids—(B.1. Hydrophilic Residues): Ser, Thr, Asn, Gln; (B.2. Aliphatic Residues): Gly, Ala, Val, Leu, Ile, Nle; (B.3. Non-polar Residues): Cys, Met, Pro, Hcy; (B.4. Aromatic Residues): Phe, Tyr, Trp.

The term "cement matrix" as used herein relates to a component of a concrete composition and includes a binder comprising any hydraulic cement. "Hydraulic cement" refers to any cement that will set and harden upon exposure to water, and includes the non-limiting examples of Portland cement, blended Portland cement (e.g. Portland blastfurnace cement, Portland flyash cement, Portland pozzolan cement, Portland silica fume cement, etc.), masonry cement, expansive cement, rapid setting and hardening cement, calcium aluminate cement, calcium sulfoaluminate cement, pozzolan-lime cement, slag-lime cement, supersulfated cement, natural cement, geopolymer cement, magnesium phosphate cement, and any mixtures and combinations thereof.

The term "concrete" as used herein encompasses construction materials comprising a cement matrix or cement-like matrix and other cementitious materials (e.g., pozzolans, aggregate, water, etc.) that are typical of concretes, mortars, and other composite materials.

The term "thermostable protein" or "thermostable" as used herein when referencing a protein or protein fragment refers to a protein that resists irreversible changes in its structure due to applied heat. Typically, as used herein, a protein (or protein fragment) can be termed "thermostable" when it exhibits the same observable characteristics (e.g., solubility, function/activity, spectroscopic signatures, etc.), at elevated temperatures (from about 50° C. to about 80° C.) as it exhibits at room temperature (e.g., about 25° C. to about 30° C.) and/or a cooled temperature (e.g., about 4° C. to about 15° C.).

The phrase "increase the strength" or "increased strength" when used to describe a concrete composition comprising BHK1 bacterial cells and/or bioremediase protein encompasses any measurable change in a characteristic of the concrete composition that can be related to an improved physical strength of the concrete composition, relative to a similar concrete composition that does not comprise BHK1 bacterial cells and/or bioremediase protein.

The terms "nucleic acid molecule encoding", "DNA sequence encoding", and "DNA encoding" refer to the order or sequence of deoxyribonucleotides along a strand of deoxyribonucleic acid. The order of these deoxyribonucleotides determines the order of amino acids along the polypeptide chain. The DNA sequence thus encodes the amino acid sequence.

An embodiment relates to an anaerobic *Thermoanaerobacter* sp. bacterial strain (BKH1) isolate from a hot spring. In an embodiment the BKH1 strain comprises a 697 nucleotide 16S ribosomal RNA sequence of:

activity of at least about 200 µg silica/mg protein to about 300 µg silica/mg protein (e.g., 200, 210, 220, 230, 240, 250, 260, 270, 280, 290, or 300 µg silica/mg protein). In yet a further embodiment the bioremediase protein, or a fragment thereof, comprises silica releasing activity of at least about 400 µg silica/mg protein to about 450 or more µg silica/mg protein (e.g., 400, 410, 420, 430, 440, or 450 or more µg silica/mg protein).

Embodiments provide active fragments of the bioremediase protein. These embodiments provide an amino acid sequence that comprises less than the full length amino acid sequence of bioremediase protein as described herein. Such a fragment can result from a truncation at the amino terminus, a truncation at the carboxy terminus, and/or an internal deletion of one or more amino acid residues from the bioremediase amino acid sequence. Naturally occurring bioremediase

```
                                                             (SEQ ID NO: 2)
ggtaagcacg gagttgagtg ccggatagcg gcggacgggg tgagtaaacg cgtgggcaaa cctaccctta agaccgggga taacacctcg aaaggggtgc taatactgga taagctcctt gtagggcatc ctatgaggag ggaaggtagc ggaagctacc gcttaaggat gggcccgcgt cccatcagct agttggtagg gtaacggcct accaaggcga cgacgggtag ccggcctgag agggtggtcg gccacactgg gactgagaca cggcccagac tcctacggga ggcagcagtg gggaatcttg cgcaatgggc gaaagcctga cgcagcgacg ccgcgtgagc gaagaaggcc ttcgggtcgt aaagctcgat agtgtgggaa gaatagatga cggtaccaca cgaaagcccc ggctaactac gtgccagcag ccgcggtaag acgtaggggg cgagcgttgt ccggaattac tgggcgtaaa gggcgcgtag gcggccactt aagtcaggtg taaaaaaccc gggctcaacc cgggggatgc acatgaaact gggtggctag agggcaggag aggggagtgg aattcccggt gtagcggtga aatgcgtaga tatcgggagg aataccagtg gcgaaggcga ctctctggac tgaccctgac gctgaggcgc gaaagcgtgg ggagcaa.
```

Accordingly, the BKH1 cell can optionally be isolated from its native environment and identified by its morphology (see FIGS. 1A & 1B), its 16S RNA sequence, and/or its biomineralization activity as described herein. The BKH1 cells can be grown under anaerobic culture conditions in water and minimal growth medium and are able to thrive at elevated temperatures.

An embodiment relates to an isolated protein (bioremediase) comprising the amino acid sequence DFPIANGERQ SPVDIDTKAV VQDPA (SEQ ID NO:1). In an embodiment the 25 amino acids of SEQ ID NO:1 are located at the amino terminus of the bioremediase protein, or an active fragment thereof. In an embodiment of this aspect the bioremediase protein migrates on 12% SDS-polyacrylamide gel at a molecular weight of about 28 kDa (FIG. 3).

In an embodiment the protein, or active fragment thereof, is thermostable from at least about 50° C. (e.g., thermostable at 55° C., 60° C., 65° C., 70° C., 75° C., 80° C., 85° C., 90° C., or to about 95° C.). In an embodiment the protein, or active fragment thereof, is thermostable from at least about 50° C. to about 80° C. (e.g., thermostable at 55° C., 60° C., 65° C., 70° C., 75° C., or to about 80° C.).

In an embodiment of this aspect the bioremediase protein, or active fragment thereof, comprises silica releasing activity of at least about 60 µg silica/mg protein to about 100 µg silica/mg protein (e.g., 65, 70, 75, 80, 85, 90, 95, or 100 µg silica/mg protein). In a further embodiment the bioremediase protein, or a fragment thereof, comprises silica releasing fragments may result from alternative RNA splicing, from in vivo processing such as removal of the leader peptide and propeptide, and/or from protease activity. In embodiments, the amino acid fragment is at least 5, 10, 20, 50, 100, or 150 amino acids in length. In embodiments, the amino acid sequence fragment comprises at least 5, at least 10, at least 20, or at least 50, 100, or 150 contiguous amino acids of the bioremediase protein.

Embodiments provide an amino acid sequence comprising a sequence at least 70%, 75%, 80%, 85%, 90%, 95%, 96%, 97%, 98%, or 99% similar to BHK1 bioremediase protein amino acid sequence, and which retains bioremediase activity. Embodiments provide an amino acid sequence comprising a sequence at least 70%, 75%, 80%, 85%, 90%, 95%, 96%, 97%, 98%, or 99% identical to BHK1 bioremediase protein amino acid sequence, and which retains bioremediase activity.

Embodiments relate to an isolated nucleic acid molecule encoding the bioremediase protein or a functional fragment thereof that comprises the amino acid sequence DFPIANGERQ SPVDIDTKAV VQDPA (SEQ ID NO:1), wherein the protein has silica releasing activity. In an embodiment of this aspect the bioremediase protein, or active fragment thereof, encoded by the nucleic acid molecule comprises silica releasing activity of at least about 60 µg silica/mg protein to about 100 µg silica/mg protein (e.g., 65, 70, 75, 80, 85, 90, 95, or 100 µg silica/mg protein). In a further embodiment the encoded bioremediase protein, or a fragment thereof, comprises silica releasing activity of at least about 200 μg silica/mg protein to about 300 μg silica/mg protein (e.g., 200, 210, 220, 230, 240, 250, 260, 270, 280, 290, or 300 μg silica/mg protein). In yet a further embodiment the encoded bioremediase protein, or a fragment thereof, comprises silica releasing activity of at least about 400 μg silica/mg protein to about 450 or more μg silica/mg protein (e.g., 400, 410, 420, 430, 440, or 450 or more μg silica/mg protein).

Embodiments provide a substantially pure nucleic acid molecule comprising a nucleotide sequence which encodes a bioremediase amino acid sequence. In embodiments, the encoded amino acid sequence comprises bioremediase activity, as described herein. In embodiments, the encoded amino acid sequence comprises a sequence at least 70%, 75%, 80%, 85%, 90%, 95%, 96%, 97%, 98%, or 99% homologous to BHK1 bioremediase protein amino acid sequence. In embodiments, the encoded amino acid sequence is at least 5, 10, 20, 50, 100, or 150 amino acids in length. In embodiments, the encoded amino acid sequence comprises at least 5, at least 10, at least 20, or at least 50, 100, or 150 contiguous amino acids of the bioremediase protein.

In an embodiment the nucleic acid molecule comprises a nucleotide sequence that is at least 70 percent identical to the nucleotide sequence encoding the bioremediase protein, or comprises a nucleotide sequence encoding polypeptides that are at least 70 percent identical to the bioremediase protein. The nucleotide sequences can be at least 75 percent, or about 80 percent, or about 85 percent, or about 90 percent, or about 95 percent identical to any of the nucleotide sequence encoding the bioremediase protein, or the nucleotide sequences that encode polypeptides that are about 75 percent, or about 80 percent, or about 85 percent, or about 90 percent, or about 95 percent identical to the bioremediase protein. Nucleic acid molecules also include fragments of the above bioremediase nucleic acid molecules which are at least about 10 contiguous nucleotides, or about 15, or about 20, or about 25, or about 50, or about 75, or about 100, or greater than about 100 contiguous nucleotides. Related nucleic acid molecules also include fragments of the above bioremediase nucleic acid molecules which encode a bioremediase amino acid sequence of at least about 25 amino acid residues, or about 50, or about 75, or about 100, or greater than about 100 amino acid residues of bioremediase protein. The isolated nucleic acid molecules include those molecules which comprise nucleotide sequences which hybridize under moderate or highly stringent conditions as defined below with any of the above nucleic acid molecules. In embodiments, the nucleic acid molecules comprise sequences which hybridize under moderate or highly stringent conditions with a nucleic acid molecule encoding a polypeptide, which polypeptide comprises the sequence as shown in SEQ ID NO:1, or with a nucleic acid fragment as defined above, or with a nucleic acid fragment encoding a polypeptide as defined above. It is also understood that related nucleic acid molecules include sequences which are complementary to any of the above nucleotide sequences.

The term "high stringency conditions" refers to those conditions that (1) employ low ionic strength reagents and high temperature for washing, for example, 0.015 M NaCl/0.0015 M sodium citrate/0.1% NaDodSO$_4$ (SDS) at 50° C., or (2) employ during hybridization a denaturing agent such as formamide, for example, 50% (vol/vol) formamide with 0.1% bovine serum albumin/0.1%. Alternatively, FICOLL® (copolymers of sucrose and epichlorhydrin for laboratory use)/0.1% polyvinylpyrrolidone/50 mM sodium phosphate buffer at pH 6.5 may be used with 750 mm NaCl, 75 mm sodium citrate at 42° C. Another example is the use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS.

The term "moderate stringency conditions" refers to conditions which generally include the use of a washing solution and hybridization conditions (e.g., temperature, ionic strength, and percent SDS) less stringent than described above. A non-limiting example of moderately stringent conditions includes overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 μl/ml denatured sheared salmon sperm DNA, followed by washing the filters in 1×SSC at about 37-50° C. Those skilled in the art will recognize how to adjust the temperature, ionic strength and other parameters as necessary in order to accommodate factors such as nucleic acid length and the like.

Embodiments provide nucleic acid constructs in the form of plasmids, vectors, transcription or expression cassettes which comprise at least one nucleic acid encoding the bioremediase protein or a functional fragment thereof that comprises the amino acid sequence DFPIANGERQ SPVDIDT-KAV VQDPA (SEQ ID NO:1). Suitable vectors can be chosen or constructed, which contain appropriate regulatory sequences, such as promoter sequences, terminator sequences, polyadenylation sequences, enhancer sequences, marker genes and other sequences as desired. Vectors can be plasmids, viral (e.g. phage, or phagemid) or any other appropriate vector. For further details see, for example, Molecular Cloning: a Laboratory Manual: 2nd edition, Sambrook et al., 1989, Cold Spring Harbor Laboratory Press.

An embodiment also relate to a recombinant cell comprising one or more of the nucleic acid constructs as described above. Suitable host cells include bacteria, mammalian cells, yeast, and baculovirus systems. In one embodiment the host cell is a bacterial cell other than BKH1. In a further embodiment, the host cell is a thermophilic bacterial cell other than BKH1.

Relatedness of Nucleic Acid Molecules and/or Amino Acid Sequences

The term "identity" refers to a relationship between the sequences of two or more amino acid sequences or two or more nucleic acid molecules, as determined by comparing the sequences. In the art, "identity" also means the degree of sequence relatedness between amino acid or nucleic acid molecule sequences, as the case may be, as determined by the match between strings of nucleotide or amino acid sequences. "Identity" measures the percent of identical matches between two or more sequences with gap alignments addressed by a particular mathematical model or computer programs (i.e., "algorithms").

The term "similarity" is a related concept, but in contrast to "identity", refers to a measure of similarity which includes both identical matches and conservative substitution matches. Since conservative substitutions apply to polypeptides and not nucleic acid molecules, similarity only deals with polypeptide sequence comparisons. If two polypeptide sequences have, for example, 10/20 identical amino acids, and the remainder are all non-conservative substitutions, then the percent identity and similarity would both be 50%. If in the same example, there are 5 more positions where there are conservative substitutions, then the percent identity remains 50%, but the percent similarity would be 75% (15/20). Therefore, in cases where there are conservative substitutions, the degree of similarity between two polypeptide sequences will be higher than the percent identity between those two sequences.

Identity and similarity of related nucleic acid molecules and polypeptides can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 19933; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M. Stockton Press, New York, 1991; and Carillo, H., and Lipman, D., SIAM J. Applied Math., 48:1073 (1988).

Non-limiting methods for determining identity and/or similarity are designed to give the largest match between the sequences tested. Methods to determine identity and similarity are codified in publicly available computer programs. Preferred computer program methods to determine identity and similarity between two sequences include, but are not limited to, the GCG program package, including GAP (Devereux, et al., Nucleic Acids Research 12:387 [1984]; Genetics Computer Group, University of Wisconsin, Madison, Wis.), BLASTP, BLASTN, and FASTA (Atschul et al., J. Molec. Biol. 215:403-410 [1990]). The BLAST X program is publicly available from the National Center for Biotechnology Information (NCBI) and other sources (BLAST Manual, Altschul] et al., NCB NLM NIH Bethesda, Md. 20894; Altschul et al., J. Mol. Biol. 215:403-410 [1990]). The well known Smith Waterman algorithm may also be used to determine identity.

By way of example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3.times. the average diagonal; the "average diagonal" is the average of the diagonal of the comparison matrix being used; the "diagonal" is the score or number assigned to each perfect amino acid match by the particular comparison matrix) and a gap extension penalty (which is usually ⅒ times the gap opening penalty), as well as a comparison matrix such as PAM 250 or BLOSUM 62 are used in conjunction with the algorithm. A standard comparison matrix (see Dayhoff et al., in: Atlas of Protein Sequence and Structure, vol. 5, supp. 3 [1978] for the PAM250 comparison matrix; see Henikoff et al., Proc. Natl. Acad. Sci USA, 89:10915-10919 [1992] for the BLOSUM 62 comparison matrix) is also used by the algorithm.

Preferred parameters for polypeptide sequence comparison include the following: Algorithm: Needleman and Wunsch, J. Mol. Biol. 48:443-453 (1970)

Comparison matrix: BLOSUM 62 from Henikoff and Henikoff, Proc. Natl. Acad. Sci. USA 89:10915-10919 (1992)

Gap Penalty: 12
Gap Length Penalty: 4
Threshold of Similarity: 0

The GAP program is useful with the above parameters. The aforementioned parameters are the default parameters for polypeptide comparisons (along with no penalty for end gaps) using the GAP algorithm.

Preferred parameters for nucleic acid molecule sequence comparison include the following:
Algorithm: Needleman and Wunsch, J. Mol Biol. 48:443-453 (1970)
Comparison matrix: matches=+10, mismatch=0
Gap Penalty: 50
Gap Length Penalty: 3

The GAP program is also useful with the above parameters. The aforementioned parameters are the default parameters for nucleic acid molecule comparisons.

Other exemplary algorithms, gap opening penalties, gap extension penalties, comparison matrices, thresholds of similarity, etc. can be used by those of skill in the art, including those set forth in the Program Manual, Wisconsin Package, Version 9, September 1997. The particular choices to be made will depend on the specific comparison to be made, such as DNA to DNA, protein to protein, protein to DNA; and additionally, whether the comparison is between given pairs of sequences (in which case GAP or BestFit are generally preferred) or between one sequence and a large database of sequences (in which case FASTA or BLASTA are preferred).

Embodiments relate to a concrete composition comprising a cement matrix and an amount of the BKH1 cells and/or an amount of the bioremediase protein. Addition of the BKH1 cell or bioremediase protein can increase the compressive strength, increase tensile strength, increase hardness and dynamic elastic-modulus, and increase compactness of the concrete when incorporated in the composition. The resulting cement composition comprises an effectively reduced permeability, a modified porosity structure, and modified microstructural properties of the matrices, and thereby increases the durability of the concrete structure. Embodiments of the concrete composition described herein can more effectively repairs cracks than normal cement-sand mixtures, and can be utilized as a self-healing concrete.

In embodiments of this aspect, the cement matrix comprises any hydraulic cement such as, for example, mortar, Portland cement, blended Portland cement (e.g. Portland blastfurnace cement, Portland flyash cement, Portland pozzolan cement, Portland silica fume cement, etc.), masonry cement, expansive cement, rapid setting and hardening cement, calcium aluminate cement, calcium sulfoaluminate cement, pozzolan-lime cement, slag-lime cement, supersulfated cement, natural cement, geopolymer cement, magnesium phosphate cement, and any mixtures and combinations thereof. In further embodiments, the cement matrix comprises Portland cement or blended Portland cement.

In embodiments of this aspect the concrete compositions comprise effective amounts of BKH1 cells and/or bioremediase. In certain embodiments, the compositions comprise an amount of BKH1 cells and/or bioremediase that is effective to increase the compressive strength of the concrete composition by about 25% relative to the strength of the concrete composition in the absence of the BKH1 cells and/or bioremediase. In further embodiments the compressive strength of the composition is increased by about 25% to about 40% (e.g., 25%, 30%, 35%, or 40%) by the addition of the BKH1 and/or bioremediase. In certain of these embodiments the amount of BKH1 cells added to the composition can vary from about 5,000 cells/mL water to about 1,000,000 cells/mL water (e.g., $5\times10^3$, $1\times10^4$, $5\times10^4$, $1\times10^5$, $5\times10^5$, or $1\times10^6$ cells/mL water). In other of these certain embodiments the amount of bioremediase added to the composition can vary from about 0.05 μg protein/g of cement to about 5 μg protein/g of cement. In further embodiments, the amount of bioremediase is from about 0.1 μg protein/g of cement to about 2.5 μg protein/g of cement (e.g., 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5 µg protein/g of cement).

The concrete compositions can comprise other components commonly found in various concretes, such as various fine and/or coarse aggregates (e.g., gravel, sand, granite, limestone, etc.) and additional binders. Aggregate components can be added amounts in typical weight ratios for concrete compositions, such as a non-limiting example of a weight ratio of about 2.0 (relative to amount of binder).

Depending on the particular use or application, the concrete composition can comprise a viscosity agent. Appropriate viscosity agents can be chosen by those of skill in the art. Some non-limiting examples of viscosity agents include methylcellulose, polyvinyl alcohol, starch, and mixture thereof. The amount of viscosity agent added to the concrete composition can vary in typical ranges for concrete compositions, such as a non-limiting example of a weight ratio of about 0.01 (relative to amount of binder).

As noted herein, the concrete composition can comprise compounds described as cement extenders (pozzolans). Examples of pozzolans include the non-limiting examples of fly ash, metakaolin, ground granulated blast furnace slag, and silica fume. Any one or combination of pozzolan compounds can be optionally included in the concrete composition described herein.

Other components can be added to the concrete compositions, such as non-limiting examples of reinforcing fibers (e.g., aramid, polyvinyl alcohol, high modulus polyethylene, and high tenacity polypropylene fibers); plasticizers; chemical agents that aid concrete flow; chemical agents that aid concrete pumping; chemical agents that delay concrete setting; chemical agents that quicken concrete setting; and other components that are found in concrete compositions.

The concrete compositions can be prepared according to any method that is commonly used for preparation of concrete. The individual components of the composition can be packaged separately and mixed (either sequentially or all at once) or the components can be packaged together in premeasured amounts. Because BKH1 and bioremediase are robust either can be packaged together with the cement matrix and other optional additives of the composition in dry form. Alternatively, the BKH1 or bioremediase can be included in a premixed package of concrete, but as a self-contained component, for example, in a meltable, soluble, or breakable container as a concentrated liquid stock. Upon mixing, the container would release the BKH1 or bioremediase, which would become evenly distributed through the composition.

Embodiments relate to a method for isolating bioremediase protein comprising SEQ ID NO:1, wherein the methods comprises: (a) culturing *Thermoanaerobacter* sp. BKH1 cells under conditions that allow for cell growth; (b) collecting the growth medium from the culturing from (a); (c) lyophilizing the growth medium from (b) to dryness; (d) dissolving the lyphilisate generated in (c) in a solvent; (e) contacting the solution generated in (d) with acetone in an amount to generate protein precipitate; (f) contacting the protein precipitate from (e) with solvent; and (g) isolating the proteins in the solution from (f) based on molecular weight; wherein the bioremediase protein comprises a molecular weight of about 28 kDa.

In embodiments of this aspect, the BKH1 cells are cultured in an anaerobic vessel with a liquid minimal growth medium. The BKH1 cells can be grown over a wide temperature range (e.g., from about 40° C. to about 65° C. or more); however it may be advantageous to grow the culture at increased temperature to help avoid contaminant growth. In other embodiments of the method steps (b) through (f) or substantial equivalents thereof can be performed using any appropriate technique or reagent as long as the objective of the step is met. For example, the contacting of the protein solution with acetone (step (e)) can be performed at room temperature or at decreased temperature (e.g., ~4° C.) as long as the protein precipitates from solution. Further alternative precipitation methods and reagents can be used instead of acetone (e.g., "salting out" with agents such as ammonium sulfate; isoelectric point precipitation; organic solvent precipitation (MeOH, EtOH, etc.); flocculation by polyelectrolytes; polyvalent metal ion precipitation; and non-ionic hydrophilic polymers (dextrans, PEGs, etc.)). Similar equivalents are recognizable by those of skill in the art for each of the steps described in the purification method.

In embodiments of this aspect, the method can further comprise standard protein purification techniques such as, for example, HPLC or FPLC chromatography using size-exclusion or affinity-based column resins. See, e.g., Sambrook, et al. 1989, Cold Spring Harbor Laboratory Press.

Embodiments relate to methods for reinforcing or repairing an existing concrete structure comprising contacting the existing concrete structure with the concrete compositions described herein.

It should be noted that the section headings are used herein for organizational purposes only, and are not to be construed as in any way limiting the subject matter described. All references cited herein are incorporated by reference in their entirety for all purposes.

The Examples that follow are merely illustrative of certain embodiments and are not to be taken as limiting.

EXAMPLES

Statistical analysis—The statistical analysis of the compressive strength test and silica release assay was performed by ANOVA using Origin version 6 Software. Significance level was noted at $P<0.05$.

Standard techniques and equipment were used in the following examples. In certain instances particular techniques and/or equipment are described for purposes of clarity.

Example 1

Isolation and Analysis of Bacterial Strain BKH1

The BKH1 bacterium was isolated from the soil of hot spring and purified through serial dilution technique from its liquid culture in the laboratory, as detailed below. The bacterium is facultative anaerobic and has rod-like morphology (see, FIG. 1). BKH1 is a Gram negative bacterium.

Soil samples were taken from the area surrounding hot springs located in Brakreshwar, India. Enrichment growth medium (40 ml) was added to sealed gas-pressure vials (100 ml capacity). Prior to inoculation, the vials were evacuated of air by introducing carbon dioxide via syringe-needle system similar to the system as described by Chattopadhyay, B. D., et al. (Chattopadhyay, B. D., et al., *Indian Journal of Experimental Biology*, (1994) 32:495-500). Inoculums of the crude soil sample (1% v/v) were added to the growth medium (pH 7.0) and incubated at 65° C. for several days in order to obtain sufficient growth of the bacterial population. A mixed population of culture developed and was used to inoculate fresh growth medium for further subculture. Pure culture of the bacterial strain was obtained using serial dilution techniques and confirmed by the scanning electron microscope (SEM) analysis of the culture (FIGS. 1A & 1B). The bacteria were unable to grow on nutritionally rich solid media (tryptic soy agar, nutrient agar, Luria-Bertani agar, and anaerobic agar). The growth parameters such as pH and temperature, the morphology and Gram's staining of the bacterium were also studied to identify some phenotypic characteristics of the isolate.

Phylogenetic analysis—Bacterial cells were collected by centrifugation of the pure cultures, and the chromosomal DNA of the bacterium was isolated by FASTDNA® (reagent kit and components for rapid isolation and purification of nucleic acids) Spin kit (Qbiogene, MP Biomedical). The 16 S-rRNA gene was amplified by using primers 27f (5'-AGA GTT TGA TCC TGG CTC AG-3'; SEQ ID NO:3) and 1492r (5'-TAC GGY TAC CTT GTT ACG ACT T-3'; SEQ ID NO:4). The amplified DNA fragment was separated on a 1% agarose gel, and was isolated from the gel and purified using the QIAQUICK® (chemical products for isolation and purification of nucleic acids) gel extraction kit (Qiagen). The purified PCR product was sequenced with the same 27f and 1492r primers. The rRNA gene sequence was determined by the dideoxy chain-termination method using the BIGDYE® (reagents for scientific use) terminator kit and ABI 310 Genetic Analyzer (Applied Biosystems). The 16S rRNA partial gene sequence (697 bases; SEQ ID NO:2) of the bacteria (named BKH1; GenBank accession number FJ177512) was aligned with sequences of other *Thermoanaerobactor* sp. contained in the Genbank database. The sequence similarity was searched using BLASTN. For the neighbor-joining analysis, distances between sequences were determined by Kimura's two-parameter model. The confidence limits of the branching were performed by Bootstrap analysis. (FIG. 2).

Example 2

Manufacture and Compressive Strength of Mortar/BKH1 Composition

Standard mortar cubes (70.6×70.6×70.6 mm$^3$) were prepared by mixing different bacterial cell concentrations (0, 10$^4$, 10$^5$ and 10$^6$ cells/ml H$_2$O) with a cement-sand mixture. Ordinary Portland cement (43 grade) and standard Ennor sand (well-graded coarse aggregate, 10 mm max. size) were used for sample preparation. The cement-to-sand ratio was 1:3 and the water-to-cement ratio was fixed at 0.4:1 for all mortar samples. For preparation, distilled water was used as a mixing water for the mortar to reduce other effects on the resulting samples. Sand and cement was thoroughly mixed with distilled water containing the required cell concentration of the microorganism. Cubes were cast and compacted using a vibration machine, and after unmolding the cubes, all samples were cured for 28 days in distilled water at room temperature (at 30° C.±2° C.) until compression testing was done. Typically, three cubes are prepared at the same time for each category of sample undergoing analysis. The experiment was repeated four times, meaning that twelve mortar samples at each bacterial cell concentration were analyzed. The samples were allowed to cure for 28 days. After the curing process, the samples were analyzed for their compressive strength as determined by a compressive strength testing machine (2000 K Newton compression testing machine). The results are summarized in Table 2, with the compressive strength averaged over all twelve samples (±S.D.). This example demonstrates that addition of various concentrations of isolated BKH1 bacteria can increase the compressive strength of mortar relative to control samples.

TABLE 2

Compression Strength of Mortar/BKH1 Compositions (28 day cure)

| Sample | Compressive Strength† (MPa) | % Strength Increase |
|---|---|---|
| Mortar + no cells/ml H$_2$O | 42.17 ± 1.36 | N.A. |
| Mortar + 10$^4$ cells/ml H$_2$O | 49.99 ± 1.85 | 18.54 |
| Mortar + 10$^5$ cells/ml H$_2$O | 52.18 ± 1.20 | 25.23 |
| Mortar + 10$^6$ cells/ml H$_2$O | 48.38 ± 2.65 | 14.72 |

†Values are mean ± S.D., (N = 12). All values are statistically significant at $P < 0.05$ Example 3

Ultrasonic Pulse Velocity of Mortar/BKH1 Composition

Additional mortar samples were prepared as described above in Example 2 in order to analyze compression wave propagation velocity characteristics. The test was performed using a Pundit Plus Ultrasonic pulse velocity meter (PC1007) according to ASTM C597-02. At least six samples (from two sets of experiment) were prepared for each mortar sample in this experiment. From the measured ultrasonic pulse velocity of mortar samples, dynamic modulus of elasticity was determined and an average value over all samples was calculated. The results are summarized in Table 3.

TABLE 3

Dynamic e-modulus of Mortar/BKH1 Compositions (28 day cure)

| Sample | Time (μs) | Velocity (m/s) | Mass (kg) | Density (10$^{-6}$ kg/m$^3$) | Dynamic e-modulus (kg m$^{-1}$s$^{-2}$) |
|---|---|---|---|---|---|
| Mortar + no cells/ml H$_2$O | 7.86 ± 0.07 | 3953 ± 11 | 0.7331 ± 0.003 | 2.08 ± 0.01 | 29.3 ± 0.4 |
| Mortar + 10$^4$ cells/ml H$_2$O | 17.72 ± 0.04 | 3984 ± 08 | 0.7291 ± 0.005 | 2.07 ± 0.02 | 29.6 ± 0.4 |
| Mortar + 10$^5$ cells/ml H$_2$O | 17.60 ± 0.05 | 4011 ± 08 | 0.7262 ± 0.003 | 2.06 ± 0.01 | 29.8 ± 0.3 |
| Mortar + 10$^6$ cells/ml H$_2$O | 17.77 ± 0.02 | 3973 ± 04 | 0.7270 ± 0.006 | 2.07 ± 0.01 | 29.6 ± 0.2 |

Values are mean ± S.D., (N = 6). All values are statistically significant at $P < 0.05$ Example 4

Isolation of Bioremediase Protein from Culture Medium

Bacterial cells (100 ml) that were grown in culture medium for 8-10 days were added to a centrifuge tube and spun to create cell-free supernatant and a cell pellet. The supernatant was removed and added to a round bottom flask where it was lyophilized to powder (Freeze dryer FD-1, Rikakikai, Toshiba). A portion of lyophilized powder (20 mg) was dissolved in 1 ml of sterile, deionized water. Ice-cold acetone (2 ml) was added to the dissolved lyophilisate in order to isolate fats from the dissolved protein fraction, and the mixture was kept at 4° C. for 2 hrs. The protein was precipitated and separated from the soluble fraction by centrifugation at 4° C. for 15 min. at 10000 g (Plasto Craft Super spin R-V/FM). The protein precipitate was suspended and washed in 1 ml ice-cold acetone, and centrifuged again to completely remove fats from the precipitated protein fraction. After removing the liquid phase and briefly air-drying, the precipitated protein was dissolved in 250 μl deionized sterile water and applied to a column (100 cm×1 cm) loaded with size-exclusion resin (SEPHADEX® (polymers for use in purification and fractionation of biomolecules) G-100)). The column was operated by gravity by using 5 mM Tris-Cl buffer (pH 6.8) with a flow rate of 0.2 ml/min. Fractions (1 ml) were collected (EYELA® (laboratory apparatus, instruments and equipment)) DC-1000 fraction collector)) and protein was detected by monitoring column eluate optical density at 280 nm (Elico SL-196 UV-Vis Spectrophotometer). The fractions containing protein were assayed for biosilicification activity using a silica-rich substrate tetraethoxyorthosilicate (TEOS), method generally detailed below. Those fractions showing biosilicification activity were pooled and concentrated (lyophilization) to 250 μl. The concentrated fraction was similarly eluted through the same SEPHADEX® G-100 column. The eluted fractions were concentrated (250 μl) by lyophilization and dialyzed in dialysis tubing cellulose membrane (25 mm×16 mm, 12 kDa MW cutoff) against deionized sterile water. The protein concentration of each eluted fraction was measured by Lowry assay. Molecular weight and purification of the protein was evaluated by SDS-PAGE (12%) using Sigma protein standards (FIG. 3). Details regarding the characteristics of the bioremediase protein at certain points in the purification scheme are detailed in Table 4.

TABLE 4

Compression Strength of Mortar/BKH1 Compositions (28 day cure)

| Sample | Total Protein (mg) | Sp. Activity (unit/mg) [†] | Protein Recovery (%) | x-Fold Purification |
|---|---|---|---|---|
| Crude Extract (media) | 2.9 | 65.4 | 100 | 1 |
| Acetone Precipitation | 1.14 | 75.6 | 39 | 1.2 |
| Sephadex G-100 (1st run) | 0.43 | 217.6 | 14.7 | 3.3 |
| Sephadex G-100 (2nd run) | 0.27 | 436.2 | 9.3 | 6.7 |

[†] One unit relates to μg of silica release per mg of protein.

Partial Amino Acid Sequence of the Purified Protein

The purified protein (100 μl; 1 μg/μl stock) was digested at 37° C. for 20 hr using endoproteinase Asp-N (10 μl; 2 pmol) (Takara Bio, Shiga, Japan). The digested protein was run on SDS-PAGE and subsequently blotted on PVDF membrane. The digested band migrating at a molecular weight of about 28 kDa was sequenced (25 amino acids from N-terminal) by Edman Degradation method. The protein bank accession number is P86277 (UniProt Knowledge) and the protein is named as "bioremediase." The 25 N-terminal amino acid sequence of the protein is: (N-term)—DFPIANGERQ SPV-DIDTKAV VQDPA (SEQ ID NO:1).

Example 5

Biosilicification Activity of Bioremediase Protein

In a reaction tube, 100 μl of the purified bioremediase enzyme (samples containing from about 20 to about 400 μg of protein) was added to 20 μl Tris-HCl buffer (20 mM, pH 8) and 50 μl TEOS (4.5 μM) and the final volume was made to 1 ml with deionized sterile water. The reaction was performed at 65° C. for 180 min and terminated by centrifugation (15000 g, 20 min). The precipitate thus obtained was washed 2 times with absolute ethanol and air-dried.

The precipitate was then dissolved in 1 ml NaOH (1 M) and the released silicic acid was quantified by the molybdate assay (see, Douglas, H. A., et al., Poly. Mater. Sci. & Engg., (2004) 90: 239-241) generally according to the following procedure: $HNO_3$ (200 μA of 5 N) and ammonium molybdate (500 μl; Laboratory standard) were added in that order to the 1 ml of NaOH (1 M) containing the precipitate. A 10% metol (N-methyl-p-aminophenol) solution (100 μl; metol:oxalic acid 1:1 v/v) was then added to the reaction mixture. By measuring the absorbance values at 405 nm, the absolute amounts of silicic acid were calculated from a calibration curve prepared using a silicon standard (Merck). The purified enzyme was also tested for biosilicification activity using Portland cement as a substrate instead of TEOS. The kinetics of the reaction was standardized for substrate concentration, pH, and temperature (FIG. 4A). Salt tolerance activity of the protein was determined in presence of $Ca^{2+}$, $Mg^{2+}$ and $Al^{3+}$ ions (FIG. 4B).

Example 6

Cement Paste and Protein Composition Compressive Strength

Control and protein-amended (both active and denatured) cement paste bars were prepared and subsequently cut into small cubes (10×10×10 $mm^3$) after several days of water curing (7, 14, 28, 60 days). For all samples water to cement ratio was kept at 0.4, and for protein-containing samples the protein concentration was varied from 0.1-2.0 μg/g (protein/cement). For each type of cured sample, 25 cubes were prepared and their compressive strengths were determined using a manual pressure bench. The averaged value (with S.D.) for the sample batch having a protein/cement ratio of 1 μg/g are presented in FIG. 5A.

Example 7

Mortar and Protein Composition Compressive Strength

Control and protein-amended (both active and denatured) mortar bars were prepared with a water-cement weight ratio of 1:2, and a cement-sand weight ratio of 1:3. Three different grain-size classes of sand particles (125-250 μm; 250-500 μm; 500-1000 μm with ratios 1:1:1) were used for mortar sample preparation. Protein was mixed with the cement at ratios from 1:1 μg/g to 1:10 μg/g (protein vs. cement). After several days of water curing (7, 14, 28, and 60 days), the bars were subsequently cut into smaller cubes (7×7×7 $mm^3$). For each type of cured sample, 25 cubes were prepared and their compressive strengths were measured using a Micro bench device. The averaged value (with S.D.) for the sample batch having a protein/mortar ratio of 1 μg/g are presented in FIG. 5B.

Example 8

Microscopic (ESEM) Analysis of Cement/Protein Composition

Cement-protein compositions were further analyzed using environmental scanning electron microscope (ESEM) imaging, which allows for determination of characteristics such as partial volumes of various components (e.g., pore, calcium hydrate silicate, and unhydrated cement). The ESEM images of cement paste control and protein amended-cement paste samples, each at a 28 day cure are presented in FIG. 6. The partial volumes of certain components are summarized in Table 5, showing the effects of curing age and protein-amendment.

TABLE 5

Compression Strength of Mortar/BKH1 Compositions (28 day cure)

| Component | Cement Paste (3 day cure) | Cement Paste (7 day cure) | Cement Paste (28 day cure) | Protein-Cement Paste (28 day cure) |
|---|---|---|---|---|
| Calcium hydrate silicate | 0.648 | 0.717 | 0.721 | 0.799 |
| Pore | 0.151 | 0.151 | 0.169 | 0.140 |
| Unhydrated Cement | 0.201 | 0.131 | 0.110 | 0.060 |

(N = 3)

Example 9

Effect of Protein/Cement Ratio on Composition Characteristics

Cement-protein compositions made according to the procedures detailed above, with protein added in an amount of 1.0 µg/g (µg protein/g cement paste) and 1.0 µg/g (µg protein/g cement paste). Samples were allowed to cure for 28 days and were analyzed for e-modulus and hardness as described in the above Examples. The results are summarized in Table 6, which includes data for a cement paste (no protein) control sample.

TABLE 6

Effect of Protein Concentration of Hardness and E-Modulus (28 day cure)

| Sample | Average Hardness (Gpa) | % of Control | Average e-modulus (Gpa) | % of Control |
|---|---|---|---|---|
| Control (cement paste only) | 0.85 ± 0.54 | 100 | 29.00 ± 13.21 | 100 |
| 1.0 µg protein/g cement | 1.45 ± 0.69 | 171 | 34.82 ± 19.76 | 120 |
| 2.0 µg protein/g cement | 1.01 ± 0.92 | 120 | 33.29 ± 16.41 | 115 |

Values are mean ± S.D., (N = 3). All values are statistically significant at $P < 0.05$ The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions, or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

REFERENCES

1. Altschul, S. F., T. L. Madden., A. A. Schaffer., J. Zhang., W. Miller, and D. J. Lipman. 1997. Gapped BLAST and PS-BLAST: a new generation of protein database search programs. *Nucleic Acids Res.* 25(17): 3389-3402.
2. ASTM C597-02: Standard test method for pulse velocity through concrete. ASTM International.
3. Bang, S. S., J. K. Galinat, and V. Ramakrishnan. 2001. Calcite Precipitation Induced by Polyurethane-Immobilized *Bacillus pasteurii*. *Enzyme Microb. Tech.* 28 (4-5): 404-409.
4. Belkova, L. N. 2005. Biomineralization in Natural Environments: The Effect of Microorganisms Inhabiting Hot Spring Water and Biomats on Mineral Formation. Abstr. 7th Geophys. Res.
5. Boskey, A. L. 2003. Biomineralization: An Overview. *Connect. Tissue Res.* 44(1): 5-9.
6. Cha, J. N., K. Shimizu., Y. Zhou., S. C. Christianssen., B. F. Chmelka., G. D. Stucky, and D. E. Morse. 1999. Silicatein Filaments and Subunits from A Marine Sponge Direct the Polymerization of Silica and Silicones In Vitro. *Proc. Natl. Acad. Sci. USA.* 96(2): 361-365.
7. Chattopadhyay, B. D., A. R. Thakur., P. C. Mangal., N. N. Puukait and A. K. Saha. 1994. Inhibitory role of aluminium in methane emission in rice field. *Ind. J. Expt. Biol.* 32: 495-500.
8. DeGraef, B., W. DeWindt. J. Dick., W. Verstraete, and N. DeBelie. 2005. Cleaning of Concrete Fouled by Lichens with the Aid of Thiobacilli. *Mat. Struct.* 38(284): 875-882.
9. Dick, J., W. DeWindt., B. DeGraef., H. Saveyn., P. VenderMeeren., N. DeBelie, and W. Verstraete. 2006. Bio-Deposition of a Calcium Carbonate Layer on Degraded Limestone by Bacillus Species. *Biodegradation* 17(4): 357-367.
10. Douglas, H. A., M. D. Daniel., E. M. Daniel, and A. A. Ilhan. 2004. Non-Peptide, Silicatein alpha Inspired Silica condensation Catalyst. Polymeric Materials: Sci. & Engg. 90: 239-.
11. Edvardsen, C. 1999. Water Permeability and Autogenous Healing of Cracks in Concrete. *ACI Mat. J.* 96(4): 448-455.
12. Ehrlich, H. L. 1995. In Marcel Dekker (ed.), Geomicrobiology. New York.
13. Felsenstein, J. 1985. Confidence limits on phylogenies: an approach using the bootstrap. *Evolution* 39: 783-791.
14. Ghosh, P., S. Mandal, and B. D. Chattopadhyay. 2006. Effect of addition of microorganism on the strength of concrete. *The Ind. Concr. J.* April: 45-48.
15. Ghosh, P., S. Mandal., B. D. Chattopadhyay, and S. Pal. 2005. Use of Microorganisms to Improve the Strength of Cement-Mortar. *Cem. Concr. Res.* 35(10): 1980-1983.
16. Ghosh, P., S. Mandal., S. Pal., G. Bandyopadhyaya, and B. D. Chattopadhyay. 2006. Development of bioconcrete material using an enrichment culture of novel thermophilic anaerobic bacteria. *Ind. J. Expt. Biol.* 44: 336-339.
17. Ghosh, S., B. D. Chattopadhyay, and S. Mandal. 2008. Use of Hot Spring Bacteria for Remediation of Cracks and Increment of Durability of Structures. *The Ind. Concr. J. September:* 11-16.
18. Ghosh, S., M. Biswas., B. D. Chattopadhyay, and S. Mandal. 2009. Microbial activity on microstructure of bacteria modified mortar. *Cem. Concr. Compos.* 31(2): 93-98.
19. Inagaki, F., Y. Motomura, and S. Ogata. 2003. Microbial Silica Deposition in Geothermal Hot Water. *App. Microbiol. Biotechnol.* 60(6): 605-612.
20. IS 8112. 1989. Specification for 43-grade Ordinary Portland Cement, Bureau of Indian Standard, New Delhi, India.
21. IS 650. 1991. Specification for standard sand from natural sources of Ennor, Tamilnadu District, India for concrete, Bureau of Indian Standard, New Delhi, India.
22. Jonkers, H. M. 2007. Self Healing Concrete: A Biological Approach, p. 195-204. In S. van der Zwaag (ed.), Self Healing Materials: An Alternative Approach to 20 Centuries of Material Science, Springer, The Netherlands.
23. Kessler, M. K., N. R. Sottos, and S. R. White. 2003. Self-Healing Structural Composite Material, Compos Part A. Appl. Sci. Manuf. 34(8): 743-753.
24. Kimura, M. 1980. A simple method for estimating evolutionary rates of base substitutions through comparative studies of nucleotide sequences. *J. Mol. Evol.* 16: 111-120.
25. Lowry, O. H., N. J. Rosebrough., A. Farr, and R. J. Randall. 1951. Protein Measurement with the Folin Phenol Reagent. *J. Biol. Chem.* 193: 265-75.
26. Mann, S. 2001. Biomineralization: Principles and Concepts. In Bioinorganic Materials Chemistry, Oxford University Press, Oxford, UK.
27. Meheta, P. K, and P. G. M. Monteiro. 1993. In Concrete: Microstructure, Properties and Methods, 2nd ed. Prentice Hall Press, New Jersey, USA.
28. Ramchandran, S. K., V. Ramakrishan, and S. S. Bang. 2001. Remediation of Concrete Using Microorganisms. *ACI. Mat. J.* 98(1): 3-9.
29. Rodriguez-Navarro, C., M. Rodriguez-Gallego., K. Ben Chekroun, and M. T. Gonzalez-Munoz. 2003. Conservation of Ornamental Stone by *Myxococcus xanthus*—Induced Carbonate Biomineralization. *Appl. Environ. Microbiol.* 69(4): 2182-2193.
30. Roose-Amsaleg, C. L., E. Garnier-Sillam, and M. Harry. 2001. Extraction and purification of microbial DNA from soil and sediment samples. *Appl. Soil Ecol.* 18(1): 47-60.

31. Saitou, N, and M. Nei. 1987. The neighbour joining method: a new method for reconstructing phylogenetic trees. *Mol. Biol. Evol.* 4: 406-425.
32. Schroder, H. C., A. Krasko., G. Le Pennec., T. Adell., M. Wiens., H. Hassanein., I. M. Muller, and W. E. G. Muller. 2003. Silicase, an enzyme which degrades biogenous amorphous silica: contribution to the metabolism of silica deposition in the demosponge *Suberites domuncula*. p. 249-268. In W. E. G. Muller (Ed), Silicon biomineralization: Biology, Biochemistry, Molecular Biology, Biotechnology, Springer-Verlag, Germany.
33. Skinner, W. C. H, and H. A. Jahren. 2003. Biomineralization, p. 117-184. In W. H. Schlesinger (ed.), Treatise on Geochemistry, vol. 8. Elsevier.
34. Vrieling, E. G., Q. Sun., T. P. M. Beelen., S. Hazelaar., W. W. C. Gieskes., R. A. van Santen, and N. A. J. M. Sommerdijk. 2005. Controlled silica synthesis inspired by diatom silicon biomineralization. *J. Nanosci. Nanotechnol.* 5: 68-78.
35. Weiner, S, and M. P. Dove. 2003. An Overview of Biomineralization Processes and the Problem of the Vital Effect in Biomineralization. Review in *Mineral Geochem.* 54: 1-29.
36. White, S. R., N. R. Sottos., P. H. Geubelle., J. S. Moore., M. R. Kessler., S. R. Sriram., E. N. Brown, and S. Viswanathan. (2001) Autonomic Healing of Polymer Composites. *Nature.* 409: 794-797.

---

SEQUENCE LISTING

<160> NUMBER OF SEQ ID NOS: 4

<210> SEQ ID NO 1
<211> LENGTH: 25
<212> TYPE: PRT
<213> ORGANISM: Artificial Sequence
<220> FEATURE:
<223> OTHER INFORMATION: Synthetic

<400> SEQUENCE: 1

Asp Phe Pro Ile Ala Asn Gly Glu Arg Gln Ser Pro Val Asp Ile Asp
1               5                   10                  15

Thr Lys Ala Val Val Gln Asp Pro Ala
            20                  25

<210> SEQ ID NO 2
<211> LENGTH: 697
<212> TYPE: DNA
<213> ORGANISM: Thermoanaerobacter sp. BKH1

<400> SEQUENCE: 2
ggtaagcacg gagttgagtg ccggatagcg gcggacgggg tgagtaaacg cgtgggcaaa      60
cctaccctta agaccgggga taacacctcg aaaggggtgc taatactgga taagctcctt     120
gtagggcatc ctatgaggag ggaaggtagc ggaagctacc gcttaaggat gggcccgcgt     180
cccatcagct agttggtagg gtaacggcct accaaggcga cgacgggtag ccggcctgag     240
agggtggtcg gccacactgg gactgagaca cggcccagac tcctacggga ggcagcagtg     300
gggaatcttg cgcaatgggc gaaagcctga cgcagcgacg ccgcgtgagc gaagaaggcc     360
ttcgggtcgt aaagctcgat agtgtgggaa gaatagatga cggtaccaca cgaaagcccc     420
ggctaactac gtgccagcag ccgcggtaag acgtaggggg cgagcgttgt ccggaattac     480
tgggcgtaaa gggcgcgtag gcggccactt aagtcaggtg taaaaaaccc gggctcaacc     540
cgggggatgc acatgaaact gggtggctag agggcaggag aggggagtgg aattcccggt     600
gtagcggtga aatgcgtaga tatcgggagg aataccagtg gcgaaggcga ctctctggac     660
tgaccctgac gctgaggcgc gaaagcgtgg ggagcaa                              697

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3

-continued agagtttgat cctggctcag                                                    20

<210> SEQ ID NO 4
<211> LENGTH: 22
<212> TYPE: DNA
<213> ORGANISM: Artificial Sequence
<220> FEATURE:
<223> OTHER INFORMATION: Synthetic

<400> SEQUENCE: 4
tacggytacc ttgttacgac tt                                                 22

FIG. 1. SEM Views Of The Bacterial Strain BKH1
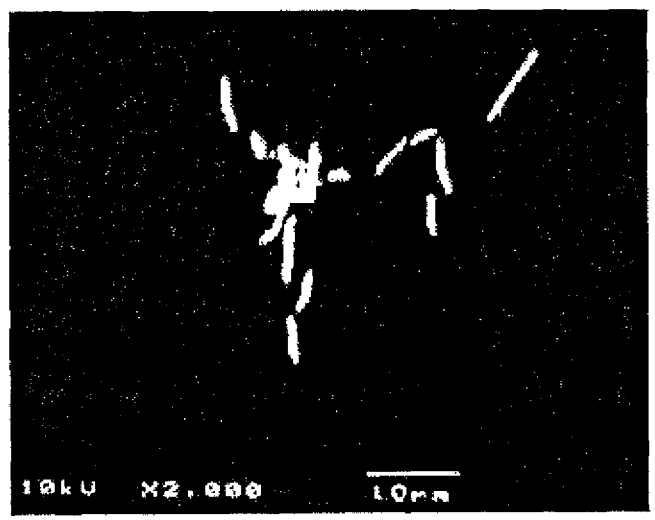
A
B
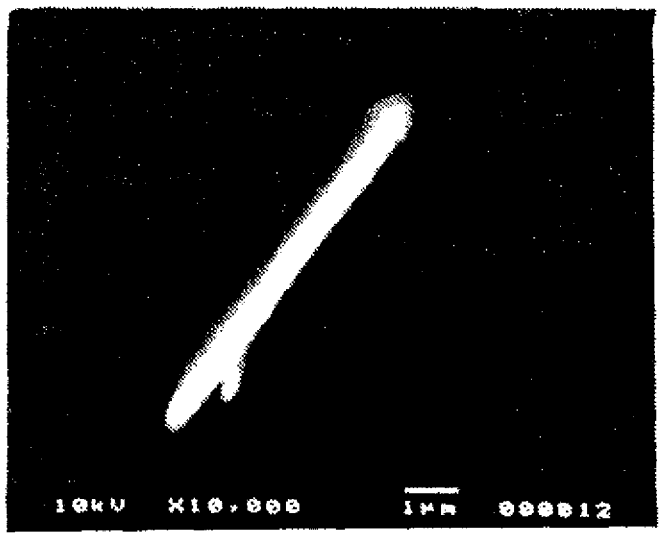

We claim:

1. A concrete composition comprising a cement matrix and an isolated protein comprising the amino acid sequence of SEQ ID NO:1, wherein the protein has silica releasing activity of about 70 µg silica/mg protein.

2. The concrete composition of claim 1, wherein the amount of protein is effective to increase the strength of the concrete composition by about 25% relative to the strength of the concrete composition in the absence of the protein.

3. The concrete composition of claim 1, wherein the amount of protein is from about 0.05 µg protein/g cement matrix to about 5.0 µg protein/g cement matrix.

4. The composition of claim 1, wherein the protein is thermostable from about 50° C. to about 80° C.

* * * * *

UNITED STATES PATENT AND TRADEMARK OFFICE
CERTIFICATE OF CORRECTION

PATENT NO.       : 8,476,039 B2
APPLICATION NO.  : 12/648297
DATED            : July 2, 2013
INVENTOR(S)      : Chattopadhyay et al.

It is certified that error appears in the above-identified patent and that said Letters Patent is hereby corrected as shown below:

On the Title Page, Item (52), under "U.S. Cl.", in Column 1, Line 1, delete "106/91; 106/314; 106/737" and insert -- 435/41; 435/174; 435/176; 106/655; 106/737; 501/122; 501/124; 424/94.1 --, therefor.

On the Title Page, under "Primary Examiner", in Column 2, Line 1, delete "Gary Nickol" and insert -- Ja'Na Hines --, therefor.

On Title Page 2, Item (56), under "OTHER PUBLICATIONS", in Column 1, Line 14, delete "Methanosarcine barkeri" and insert -- Methanosarcina barkeri --, therefor.

On Title Page 2, Item (56), under "OTHER PUBLICATIONS", in Column 1, Line 45, delete "Is 8112." and insert -- IS 8112. --, therefor.

On Title Page 2, Item (56), under "OTHER PUBLICATIONS", in Column 1, Line 47, delete "Is 650." and insert -- IS 650. --, therefor.

On Title Page 2, Item (56), under "OTHER PUBLICATIONS", in Column 2, Line 6, delete ""Remeditation" and insert -- "Remediation --, therefor.

On Title Page 2, Item (56), under "OTHER PUBLICATIONS", in Column 2, Line 7, delete "ACI." and insert -- ACI --, therefor.

On Title Page 2, Item (56), under "OTHER PUBLICATIONS", in Column 2, Line 37, delete "Biol,1970," and insert -- Biol, 1970, --, therefor.

Signed and Sealed this
Twelfth Day of November, 2013

Teresa Stanek Rea
*Deputy Director of the United States Patent and Trademark Office*

CERTIFICATE OF CORRECTION (continued)
U.S. Pat. No. 8,476,039 B2

In the Drawings

In Fig. 4B, Sheet 5 of 8, delete "Concencentration" and insert -- Concentration --, therefor. (See Attached Sheet)

In the Specification

In Column 2, Line 57, delete "lyphilisate" and insert -- lyophilisate --, therefor.

In Column 5, Line 10, delete "calcium hydrate silicate" and insert -- calcium silicate hydrate --, therefor.

In Column 6, Line 43, delete "flyash" and insert -- fly ash --, therefor.

In Column 6, Line 67, delete "BHK1" and insert -- BKH1 --, therefor.

In Column 7, Line 4, delete "BHK1" and insert -- BKH1 --, therefor.

In Column 8, Line 50, delete "BHK1" and insert -- BKH1 --, therefor.

In Column 8, Line 54, delete "BHK1" and insert -- BKH1 --, therefor.

In Column 9, Line 16, delete "BHK1" and insert -- BKH1 --, therefor.

In Column 11, Line 31, delete "Altschul] et al., NCB" and insert -- Altschul et al., NCBI --, therefor.

In Column 11, Line 57, delete "(1970)" and insert -- (1970). --, therefor.

In Column 11, Line 60, delete "(1992)" and insert -- (1992). --, therefor.

In the Claims

In Column 13, Line 54, delete "lyphilisate" and insert -- lyophilisate --, therefor.

In Column 18, Line 9, delete "239-241)" and insert -- 239-240) --, therefor.

In Column 18, Line 10, delete "(200 μA" and insert -- (200 μl --, therefor.

In Column 22, Line 4, delete "239-." and insert -- 239-240. --, therefor.

In Column 22, Line 58, delete "Remeditation" and insert -- Remediation --, therefor.

In Column 22, Line 59, delete "ACI." and insert -- ACI --, therefor.

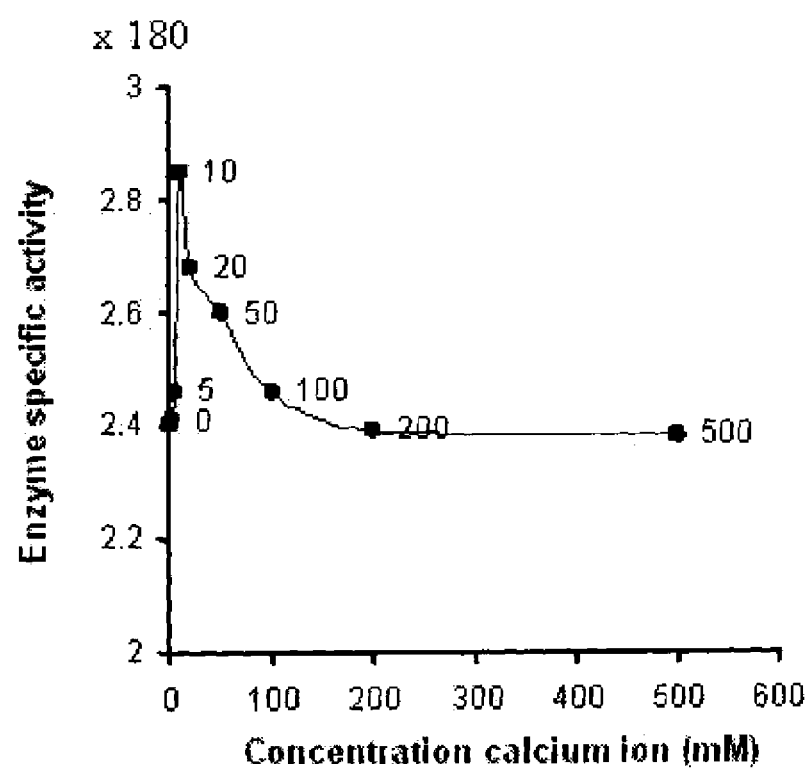
Fig. 4B. Salt tolerance activity of the purified protein

UNITED STATES PATENT AND TRADEMARK OFFICE
CERTIFICATE OF CORRECTION

| | | |
|---|---|---|
| PATENT NO. | : 8,476,039 B2 | Page 1 of 1 |
| APPLICATION NO. | : 12/648297 | |
| DATED | : July 2, 2013 | |
| INVENTOR(S) | : Chattopadhyay et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 655 days.

Signed and Sealed this
Twenty-seventh Day of January, 2015

Michelle K. Lee
*Deputy Director of the United States Patent and Trademark Office*

UNITED STATES PATENT AND TRADEMARK OFFICE
CERTIFICATE OF CORRECTION

PATENT NO. : 8,476,039 B2
APPLICATION NO. : 12/648297
DATED : July 2, 2013
INVENTOR(S) : Chattopadhyay et al.

Page 1 of 2

It is certified that error appears in the above-identified patent and that said Letters Patent is hereby corrected as shown below:

In the Drawings:

Fig. 1, Sheet 1 of 8, delete "FIGURE" and insert -- FIG. --, therefor. (See Attached Sheet)

Fig. 2, Sheet 2 of 8, delete "FIGURE" and insert -- FIG. --, therefor.

Fig. 3, Sheet 3 of 8, delete "FIGURE" and insert -- FIG. --, therefor.

Fig. 6, Sheet 8 or 8, delete "FIGURE" and insert -- FIG. --, therefor.

In the Specification:

Column 9, Line 63, delete "epichlorhydrin" and insert -- epichlorohydrin --, therefor.

Column 12, Line 4, delete "(1970)" and insert -- (1970). --, therefor.

Column 12, Line 39, delete "flyash" and insert -- fly ash --, therefor.

Column 15, Line 25, delete "Thermoanaerobactor" and insert -- Thermoanaerobacter --, therefor.

Column 19, Lines 2-3, delete "calcium hydrate silicate," and insert -- calcium silicate hydrate, --, therefor.

Signed and Sealed this
Second Day of February, 2016

Michelle K. Lee
*Director of the United States Patent and Trademark Office*